United States Patent
Bigi et al.

(10) Patent No.: US 11,111,198 B2
(45) Date of Patent: Sep. 7, 2021

(54) HYDROFORMYLATION PROCESS

(71) Applicant: Dow Technology Investments LLC, Midland, MI (US)

(72) Inventors: Marinus A. Bigi, Pearland, TX (US); Michael A. Brammer, Freeport, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 16/759,879

(22) PCT Filed: Nov. 29, 2018

(86) PCT No.: PCT/US2018/062985
§ 371 (c)(1),
(2) Date: Apr. 28, 2020

(87) PCT Pub. No.: WO2019/112866
PCT Pub. Date: Jun. 13, 2019

(65) Prior Publication Data
US 2021/0179523 A1    Jun. 17, 2021

Related U.S. Application Data

(60) Provisional application No. 62/595,868, filed on Dec. 7, 2017.

(51) Int. Cl.
*C07C 45/50* (2006.01)
*C07C 45/86* (2006.01)
*B01J 31/18* (2006.01)

(52) U.S. Cl.
CPC ............. *C07C 45/50* (2013.01); *B01J 31/185* (2013.01); *C07C 45/86* (2013.01); *B01J 2231/321* (2013.01); *B01J 2531/822* (2013.01)

(58) Field of Classification Search
CPC ................................. C07C 45/50; C07C 45/86
See application file for complete search history.

(56) References Cited

U.S. PATENT DOCUMENTS

| | | |
|---|---|---|
| 4,388,476 A | 6/1983 | Cooper |
| 4,599,206 A | 7/1986 | Billig et al. |
| 4,774,361 A | 9/1988 | Maher et al. |
| 7,232,931 B2 | 6/2007 | Toetsch et al. |
| 8,404,903 B2 | 3/2013 | Cox et al. |

FOREIGN PATENT DOCUMENTS

| | | |
|---|---|---|
| JP | 03885414 A | 12/2006 |
| WO | 2016/089602 A1 | 6/2016 |

OTHER PUBLICATIONS

Finke, Coordination Chemistry Reviews, 251 (2007) 1075-1100.
PCT/US2018/062985, International Search Report and Written Opinion dated Jan. 29, 2019.
PCT/US2018/062985, International Preliminary Report on Patentability dated Jun. 18, 2020.

*Primary Examiner* — Sikarl A Witherspoon

(57) ABSTRACT

The present invention relates to hydroformylation processes for producing aldehydes. In some embodiments, the process comprises contacting in a reaction zone reactants comprising an olefin, hydrogen and CO in the presence of a rhodium-organophosphite based catalyst, optionally with free organophosphite ligand, and 0.1 to 3 weight percent, based on the total weight of the fluid in the reaction zone, of certain polymers specified herein, such that the solubility of the polymer in the aldehyde is greater than or equal to 1 weight percent at 40° C.

9 Claims, No Drawings

HYDROFORMYLATION PROCESS

FIELD

The present invention relates to hydroformylation processes and in particular, to hydroformylation processes that utilize recycle streams with solubilized rhodium-phosphite complex catalysts.

BACKGROUND

It is known in the art that aldehydes may be readily produced by reacting an olefinically unsaturated compound with carbon monoxide and hydrogen in the presence of a solubilized rhodium-phosphite ligand complex catalyst and that a preferred type of such processes involves continuous hydroformylation and recycling of the catalyst, such as disclosed, e.g., in U.S. Pat. No. 4,599,206. Often, such processes utilize liquid recycle, although gas recycle hydroformylation processes are also feasible.

Despite the benefits attendant with such solubilized rhodium-phosphite complex catalyzed liquid recycle hydroformylation processes, under certain circumstances, the rhodium in some rhodium-phosphite complex catalysts may precipitate from solution during hydroformylation as rhodium metal or in the form of clusters of rhodium.

The use of stripping gas vaporizers including those with added CO to mitigate rhodium losses during the vaporization stages have been reported (see, e.g., U.S. Pat. No. 8,404,903 and PCT Publication WO2016/089602). However, such systems require significant capital outlay and are not readily retrofitted to an existing facility.

The use of polymeric additives containing polar functional groups, such as groups selected from the class consisting of amide, ketone, carbamate, urea, and carbonate radicals, has been found to mitigate the rhodium loss as reported in U.S. Pat. No. 4,774,361. However, these polar polymeric additives are insoluble in many hydroformylation catalyst solutions rendering them ineffective in these applications.

It would be desirable to have alternative approaches for mitigating rhodium loss in hydroformylation processes utilizing a recycle stream of rhodium-phosphite complex catalysts.

SUMMARY

The present invention has advantageously discovered an alternative approach for mitigating rhodium loss in hydroformylation processes that utilize a recycle stream of rhodium-phosphite complex catalysts. Some embodiments of the present invention advantageously provide hydroformylation processes with an improved solubilized rhodium-phosphite complex catalyzed liquid recycle operation of olefins ($C_4$ and higher) wherein precipitation of the rhodium in the complex catalyst solution during liquid recycle is minimized or prevented. In particular, and as set forth in more detail below, the present invention utilizes certain organic polymers in the process to minimize or prevent such precipitation. In particular, in some embodiments, such precipitation can be minimized by carrying out the distillative recovery of the aldehyde product in the presence of certain organic polymers described herein.

In one aspect, a hydroformylation process for producing an aldehyde comprises contacting in a reaction zone reactants comprising an olefin, hydrogen and CO in the presence of a rhodium-organophosphite based catalyst, optionally with free organophosphite ligand, and 0.1 to 3 weight percent, based on the total weight of the fluid in the reaction zone, of at least one polymer having the structure of Formula (I) or Formula (II), respectively:

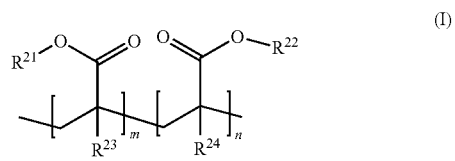

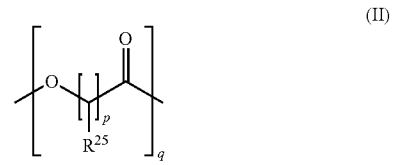

wherein $R^{21}$ and $R^{22}$ are the same or different $C_1$ to $C_{16}$ alkyl or alkyl-substituted aryl moieties and m, n, and q are positive numbers or zero whose sum is greater than 50 and p is 3 to 6 inclusive, wherein the polymer average molecular weight is equal to or above 10,000, wherein $R^{23}$ and $R^{24}$ are H or a $C_1$ to $C_4$ alkyl moiety, wherein $R^{25}$ is H or a $C_1$ to $C_{16}$ alkyl moiety, and wherein $R^{25}$ can be the same or different for each p moiety within Formula (II), such that the solubility of the polymer in the aldehyde is greater than or equal to 1 weight percent at 40° C. In some embodiments, $R^{23}$ and $R^{24}$ are methyl. In some embodiments, the polymer comprises poly(butyl methacrylate-co-methyl methacrylate) or poly (isobutylmethacrylate). In some embodiments, the polymer comprises polycaprolactone.

These and other embodiments are discussed in more detail in the Detailed Description below.

DETAILED DESCRIPTION

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the terms "ppm" and "ppmw" are used interchangeably and mean parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the terms "hydroformylation" or "hydroformylation process" are contemplated to include, but are not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds, which may be dissolved and/or suspended, formed in the reaction. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an acid removal system such as an extractor or other immiscible fluid contacting system, (g) a treated or untreated fluid returned to a reaction zone or separation zone, (h) a fluid in an external cooler, and (i) ligand decomposition products and components derived from them, such as oxides, sulfides, salts, oligomers, and the like.

"Organomonophosphite ligands" are compounds containing a single phosphorous atom bound to three oxygen atoms; the three oxygen atoms are each additionally bound to carbon moieties. Illustrative examples include, but are not limited to monoorganophosphite, diorganophosphite, triorganophosphite compounds, examples of which include: tris (2,4-di-t-butylphenyl)phosphite, 4,8-di-tert-butyl-6-(2-(tert-butyl)-4-methoxyphenyl)-2,10-dimethoxydibenzo[d,f][1,3,2]dioxaphosphepine, and the like.

The term "free ligand" means ligand that is not complexed with (or bound to) the metal, e.g., metal atom, of the complex catalyst.

For the purposes of this invention, the terms "heavy byproducts" and "heavies" are used interchangeably and refer to liquid byproducts that have a normal boiling point that is at least 25° C. above the normal boiling point of the desired product of the hydroformylation process. Such materials are known to form in hydroformylation processes under normal operation through one or more side reactions, including for example, by aldol condensation.

For the purpose of this invention, the term "dimer" when referring to heavy byproducts from a hydroformylation reaction refers to heavy byproducts derived from two molecules of aldehyde. Likewise the term "trimer" when referring to heavy byproducts from a hydroformylation reaction refers to heavy byproducts derived from three molecules of aldehyde.

For the purposes of this invention, the terms "separation zone" and "vaporizer" are used interchangeably and refer to a separation device wherein the product aldehyde is typically volatilized overhead, condensed and collected, while the non-volatile concentrated effluent (tails, or vaporizer tails) containing the homogeneous catalyst is returned to one or more of the reactors. The vaporizer temperature is typically higher than the reactor temperature, and may optionally be operated at reduced pressure. In one embodiment, the vaporizer features flowing gas of varying composition that aids in product removal and optionally helps stabilize the catalyst ("strip gas vaporizer"). Other separation zone processes such as liquid/liquid extraction or membrane filtration may also be employed.

In general, the present invention is directed to hydroformylation processes that improve the rhodium stability of any solubilized rhodium-phosphite catalyzed, liquid recycle hydroformylation process of olefins and in particular, higher olefins, which may experience such rhodium precipitation from solution. Embodiments of the present invention carry out the distillative recovery of the aldehyde product from a reaction fluid containing the rhodium-phosphite complex catalyst and aldehyde product in the presence of certain organic polymers as defined further herein.

In some embodiments, a hydroformylation process for producing an aldehyde comprises contacting in a reaction zone reactants comprising an olefin, hydrogen and CO in the presence of a rhodium-organophosphite based catalyst, optionally with free organophosphite ligand, and 0.1 to 3 weight percent, based on the total weight of the fluid in the reaction zone, of at least one polymer having the structure of Formula (I) or Formula (II), respectively:

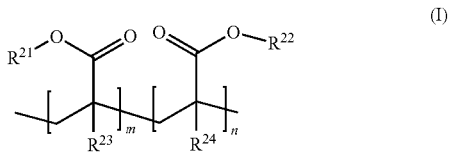

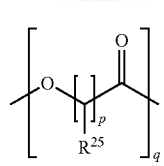

(II)

wherein $R^{21}$ and $R^{22}$ are the same or different $C_1$ to $C_{16}$ alkyl or alkyl-substituted aryl moieties and m, n, and q are positive numbers or zero whose sum is greater than 50 and p is 3 to 6 inclusive, wherein the polymer average molecular weight is equal to or above 10,000, wherein $R^{23}$ and $R^{24}$ are H or a $C_1$ to $C_4$ alkyl moiety, wherein $R^{25}$ is H or a $C_1$ to $C_{16}$ alkyl moiety, and wherein $R^{25}$ can be the same or different for each p moiety within Formula (II), such that the solubility of the polymer in the aldehyde is greater than or equal to 1 weight percent at 40° C. In some embodiments, $R^{23}$ and $R^{24}$ are methyl. In some embodiments, the polymer comprises poly(butyl methacrylate-co-methyl methacrylate) or poly (isobutylmethacrylate). In some embodiments, the polymer comprises polycaprolactone. The olefin is $C_4$ and higher, in some embodiments. In some embodiments, the olefin is $C_8$ or higher. In some embodiments, the polymer having the structure of Formula (I) or Formula (II) is present in the separation zone.

Embodiments of such processes can reduce or prevent the rate of rhodium loss in reaction fluids in a hydroformylation process. In some embodiments, the rate of rhodium loss from the reaction fluid in the hydroformylation process is less than the rate of rhodium loss in a reaction fluid in a hydroformylation process without the polymer additive. In some embodiments, the rate of rhodium loss from the reaction fluid in the hydroformylation process is at least 20% less than the rate of rhodium loss in a reaction fluid in a hydroformylation process without the polymer additive.

Illustrative solubilized rhodium-phosphite complex catalyzed, liquid recycle hydroformylation process in which such rhodium precipitation may occur include such processes as described e.g. in U.S. Pat. Nos. 4,482,749, 4,599,206, 4,668,651, 4,748,261, and 4,769,498.

In general such hydroformylation reactions involve the production of aldehydes by reacting an olefinic unsaturated compound with carbon monoxide and hydrogen in the presence of a solubilized rhodium-phosphite complex catalyst in a liquid medium that also contains a solvent for the catalyst, and free phosphite ligand (i.e. ligand that is not complexed with the rhodium metal in the active complex catalyst). The recycle procedure generally involves withdrawing a portion of the liquid reaction medium containing the catalyst and aldehyde product from the hydroformylation reaction zone, either continuously or intermittently, and distilling the aldehyde product therefrom in one or more stages under normal, reduced or elevated pressure, as appropriate, in a separate distillation zone in order to recover the aldehyde product and other volatile materials in vaporous form, the non-volatilized rhodium catalyst containing residue being recycled to the reaction zone. Condensation of the volatilized materials, and separation and recovery thereof, e.g. by distillation, can be carried out in any conventional manner, the aldehyde product being passed on for further purification if desired and any recovered reactants e.g. olefinic starting material and syngas recycled in any desired manner to the hydroformylation zone. Likewise, the recovered non-volatilized rhodium catalyst containing residue can be recycled with or without further treatment to the hydroformylation zone in any conventional manner desired. Accordingly, the general hydroformylation processes in which embodiments of the present invention may be implemented correspond to any of the known processing techniques heretofore employed in conventional gas or liquid catalyst recycle hydroformylation reactions.

Illustrative rhodium-phosphite complex catalysts employable in such hydroformylation reactions encompassed by this invention may include, without limitation, those disclosed in the above mentioned patents and applications. In general such catalysts may be pre-formed or formed in situ as described in such references and consist essentially of rhodium in complex combination with an organophosphite ligand. It is believed that carbon monoxide is also present and complexed with the rhodium in the active species. The active catalyst species may also contain hydrogen directly bonded to the rhodium.

Illustrative organophosphite ligands that may be employed as the organophosphite ligand complexed to the rhodium catalyst and/or free organophosphite ligand in such hydroformylation reactions encompassed by this invention may include a variety of tertiary organophosphites, such as preferably diorganophosphites of the formula (III) wherein, $R^1$ represents a divalent organic radical and W represents a substituted or unsubstituted monovalent hydrocarbon radical.

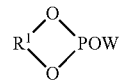

(III)

Representative divalent radicals represented by $R^1$ in Formula (III) above include those wherein R may be a divalent acyclic radical or a divalent aromatic radical. Illustrative divalent acyclic radicals are e. g. alkylene, alkylene-oxyalkylene, alkylene-$N_X$-alkylene wherein is hydrogen or a monovalent hydrocarbon radical, alkylene-S-alkylene, and cycloalkylene radicals; and the like, such as disclosed more fully e.g. in U.S. Pat. Nos. 3,415,906 and 4,567,306, and the like. Illustrative divalent aromatic radicals are e.g. arylene, bi-arylene, arylene-alkylene, arylene alkylene-arylene, arylene-oxy-arylene, arylene-oxy-alkylene, arylene-$N_X$-arylene and arylene $N_X$-alkylene wherein X is hydrogen or a monovalent hydrocarbon radical, arylene-S-alkylene, and arylene-S-arylene radicals; and the like. More preferably $R^1$ is a divalent aromatic radical.

Representative of a more preferred class of tertiary diorganophosphites are diorganophosphites of the formula (IV) wherein W is a substituted or unsubstituted monovalent hydrocarbon radical, Ar is a substituted or unsubstituted aryl radical, each Ar being the same or different, each y individually has a value of 0 or 1, Q is a divalent bridging group selected from the group consisting of —$CR^3R^4$—, —O—, —S—, —$NR^5$—, $SiR^6R^7$— and —CO—, wherein each $R^3$ and $R^4$ is independently selected from the group consisting of hydrogen, alkyl radicals having 1 to 12 carbon atoms, phenyl, tolyl and anisyl, wherein each $R^5$, $R^6$ and $R^7$ are independently hydrogen or a methyl radical, and n has a value of 0 or 1. Formula (IV) type diorganophosphites are described in greater detail, e.g., in U.S. Pat. Nos. 4,599,206 and 4,717,775.

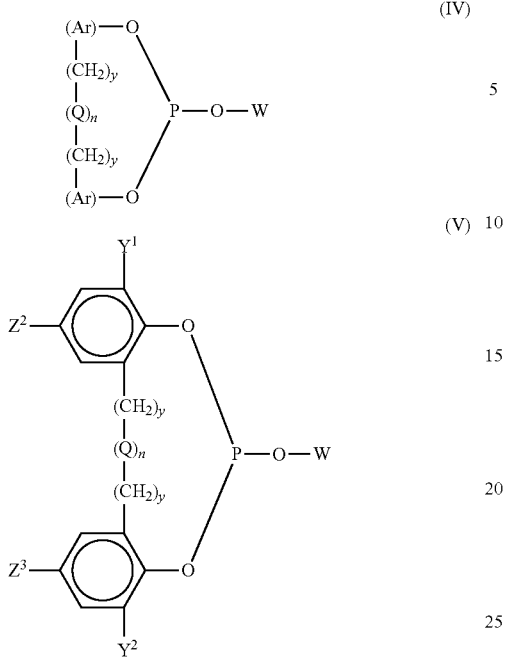

Among the more preferred diorganophosphites are those of the formula (V) wherein Q is —$CR^1R^2$— and each $R^1$ and $R^2$ radical individually represents a radical selected from the group consisting of hydrogen and alkyl; wherein each y individually has a value of 0 or 1, and n has a value of 0 to 1; wherein W represents in unsubstituted or substituted monovalent hydrocarbon radical selected from the group consisting of alkyl radicals having from 1 to 36 carbon atoms, (such as primary, secondary and tertiary alkyl radicals e.g. methyl, ethyl, n-propyl, isopropyl, butyl, sec-butyl, t-butyl, t-butylethyl, t butylpropyl, n-hexyl, amyl, sec-amyl, t-amyl, iso-octyl, 2-ethylhexyl, decyl, octadecyl, and the like) as well as, aryl radicals, such as alpha-naphthyl, beta-naphthyl, and aryl radicals of the formula (VI):

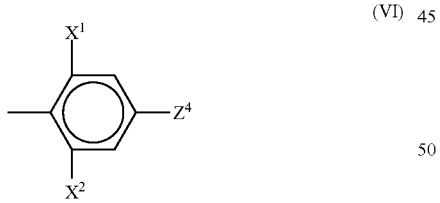

and wherein each $X^1$, $X^2$, $Y^1$, $Y^2$, $Z^2$, $Z^3$, and $Z^4$ group individually represents a radical selected from the group consisting of hydrogen, an alkyl radical having from 1 to 8 carbon atoms, substituted or unsubstituted aryl, alkaryl, aralkyl and alicyclic radicals (e.g. phenyl, benzyl, cyclohexyl, 1-methylcyclohexyl, and the like), hydroxy (—OH), and an ether (i.e oxy) radical such as —$OR^8$ wherein $R^8$ is an alkyl radical of 1 to 18 carbon atoms. Among other diorganophosphites are those of Formula (V) above as described in U.S. Pat. Nos. 4,599,206, 4,717,775, and WO 2016/087301.

Another group of tertiary organophosphites that may be employed in such hydroformylation reactions encompassed by this invention are tertiary mono organophosphites of the formula (VII) wherein $Z^5$ represents a trivalent organic radical, such as described in greater detail e.g. in U.S. Pat. No. 4,567,306.

Finally another group of tertiary organophosphites that may be employed in such hydroformylation reactions encompassed by this invention include triorganophosphites, such as tris(2,4-di-t-butylphenyl)phosphite, tris(ortho-phenyl) phenyl phosphite, tris(ortho-methyl)phenyl phosphite, tris (ortho-t-butyl)phenyl phosphite, and the like. Such triorganophosphites are described in greater detail, for example, in U.S. Pat. Nos. 3,527,809, 4,717,775 and 9,737,884.

Thus the organophosphite ligand employable in the hydroformylation reactions encompassed by this invention as the organophosphite ligand of the rhodium-organophosphite complex catalyst and/or as the free organophosphite ligand present in the hydroformylation reaction medium and liquid solutions throughout the hydroformylation process may be a tertiary organic phosphite ligand selected from the group consisting of monoorganophosphites, diorganophosphites, and triorganophosphites, such as described above. Mixtures of tertiary organic phosphite ligands may be employed as well.

The hydroformylation process encompassed by this invention may be carried out in any excess amount of free organophosphite ligand desired, e. g. at least one mole of free organophosphite ligand per mole rhodium present in the reaction medium on up to 100 moles of free organophosphite ligand or higher if desired. In general amounts of organophosphite ligand of from about 4 to about 50 moles per mole rhodium present in the reaction medium should be suitable for most purposes, said amounts being the sum of both the amount of organophosphite that is bound (complexed) to the rhodium present and the amount of free (non-complexed) organophosphite ligand present. Of course, if desired, make-up organophosphite ligand can be supplied to the reaction medium of the hydroformylation process, at any time and in any suitable manner, to maintain a predetermined level of free ligand in the reaction medium. Moreover, it is to be understood that while the organophosphite ligand of the rhodium-organophosphite complex catalyst and excess free organophosphite ligand in a given process are both normally the same, different organophosphite ligands, as well as, mixtures of two or more different organophosphite ligands may be employed for each purpose in any given process, if desired.

The amount of rhodium-organophosphite complex catalyst present in the reaction medium of a given hydroformylation process encompassed by this invention need only be that minimum amount necessary to provide the given rhodium concentration desired to be employed and which will furnish the basis for at least that catalytic amount of rhodium necessary to catalyze the particular hydroformylation process involved such as disclosed e.g. in the above-mentioned patents and applications. In general, rhodium concentrations in the range of from about 10 ppm to about 1000 ppm, calculated as free rhodium, in the hydroformylation reaction medium should be sufficient for most processes, while it is generally preferred to employ from about 10 to 500 ppm of rhodium and more preferably from 25 to 350 ppm to rhodium.

The olefinic starting material reactants that may be employed in the hydroformylation reactions encompassed by of this invention can be terminally or internally unsaturated and be of straight-chain, branched-chain or cyclic structure, such as disclosed e.g. in the above-mentioned patents and applications. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, alkyl, haloalkyl, and the like. Illustrative olefinic unsaturated compounds include alpha olefins, internal olefins, alkyl alkenoates, alkenyl alkanoates, alkenyl alkyl ethers, alkenols, and the like, e.g. ethylene, propylene, 1-butene, 1-pentene, 1-hexene, 1-octene, 1-decene, 1-dodecene, 1-octadecene, 2-butene, isobutylene, 2-methylbutene, 2-hexene, 3-hexene, 2-heptene, cyclohexene, propylene dimers, propylene trimers, propylene tetramers, butene dimers, butene trimers, 2-ethyl-1-hexene, styrene, 3-phenyl-1-propene, 1,4-hexadiene, 1,7-octadiene, 3-cyclohexyl-1-butene, and the like. Of course, it is understood that mixtures of different olefinic starting materials can be employed, if desired. Embodiments of the present invention can be particularly useful in the hydroformylation of $C_4$ and higher olefins. Thus, in some embodiments, the olefinic unsaturated starting materials are alpha olefins containing from 4 to 20 carbon atoms, and internal olefins containing from 4 to 20 carbon atoms as well as starting material mixtures of such alpha olefins and internal olefins.

As noted above hydroformylation reactions encompassed by this invention are also conducted in the presence of an organic solvent for the rhodium-phosphite complex catalyst. Any suitable solvent which does not unduly adversely interfere with the intended hydroformylation process can be employed. Illustrative suitable solvents for rhodium catalyzed hydroformylation processes include those disclosed e.g. in the above mentioned patents and applications. Of course mixtures of one or more different solvents may be employed if desired. Most preferably the solvent will be one in which the olefinic starting material, hydroformylation catalyst and organic polymer additive employed herein are all substantially soluble. In general, it is preferred to employ aldehyde compounds corresponding to the aldehyde products desired to be produced and/or higher boiling aldehyde liquid condensation by products as the primary solvent such as the higher boiling aldehyde liquid condensation by-products that are produced in situ during the hydroformylation process. Indeed, while one may employ any suitable solvent at the startup of a continuous process, the primary solvent will normally eventually comprise both aldehyde products and higher boiling aldehyde liquid condensation by products due to the nature of such continuous processes. Such aldehyde condensation by-products can also be preformed if desired and used accordingly. These condensation products contain polar moieties such as esters and alcohols yet do not appear to stabilize the rhodium catalysts from generating clusters and colloids. Of course, the amount of solvent employed is not critical to the subject invention and need only be that amount sufficient to provide the reaction medium with the particular rhodium concentration desired for a given process. In general, the amount of solvent when employed may range from about 5 percent by weight up to about 95 percent by weight or more based on the total weight of the reaction medium.

The hydroformylation reaction conditions that may be employed in the hydroformylation processes encompassed by this invention may include any suitable continuous liquid catalyst recycle hydroformylation conditions heretofore disclosed in the above-mentioned patents and applications. For instance, the total gas pressure of hydrogen, carbon monoxide and olefinic unsaturated starting compound of the hydroformylation process may range from about 7 to about 69000 kPa(a). In general, however, it is preferred that the process be operated at a total gas pressure of hydrogen, carbon monoxide and olefinic unsaturated starting compound of less than about 10300 kPa(a) and more preferably less than about 3400 kPa(a). The minimum total pressure being limited predominately by the amount of reactants necessary to obtain a desired rate of reaction. More specifically the carbon monoxide partial pressure of the hydroformylation process of this invention is preferably from about 7 to about 830 kPa(a), and more preferably from about 21 to about 620 kPa(a), while the hydrogen partial pressure is preferably about 100 to about 1100 kPa(a) and more preferably from about 200 to about 690 kPa(a). In general $H_2$:CO molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150° C. In general, hydroformylations at reaction temperatures of about 50° C. to about 120° C. are preferred for all types of olefinic starting materials; higher temperatures are considered to be less desirable, due to possible catalyst activity decline as disclosed e.g. in U.S. Pat. No. 4,599,206.

Moreover as noted herein, the solubilized rhodium-phosphite complex catalyzed continuous hydroformylation process employable in this invention involves a liquid catalyst recycle procedure. Such types of liquid catalyst recycle procedures are known as disclosed e.g. in the above-mentioned patents and applications, and thus need not be particularly detailed herein, since any such conventional catalyst recycle procedures may be employed by this invention. For instance in such liquid catalyst recycle procedures it is common place to continuously remove a portion of the liquid reaction product medium, containing e.g. the aldehyde product, the solubilized rhodium-phosphite complex catalyst, free phosphite ligand, and organic solvent, as well as by-products produced in situ by the hydroformylation, e.g. aldehyde condensation by-products etc., and unreacted olefinic starting material, carbon monoxide and hydrogen (syn gas) dissolved in said medium, from the hydroformylation reactor, to a distillation zone, e.g. a vaporizer/separator wherein the desired aldehyde product is distilled in one or more stages under normal, reduced or elevated pressure as appropriate and separated from the liquid medium. The vaporized or distilled desired aldehyde product so separated may then be condensed and recovered in any conventional manner as discussed above. The remaining non-volatilized liquid residue which contains rhodium-phosphite complex catalyst, solvent, free phosphite ligand and usually some aldehyde product is then recycled back, with or without further treatment as desired, along with whatever by-product and non-volatilized gaseous reactants that might still also be dissolved in said recycled liquid residue, in any conventional manner desired, to the hydroformylation reactor, such as disclosed e.g. in the above-mentioned patents and applications. Moreover the reactant gases so removed by such distillation from the vaporizer may also be recycled back to the reactor if desired.

The distillation and separation of the desired aldehyde product from the rhodium-phosphite complex catalyst containing product solution may take place at any suitable temperature desired. In general it is recommended that such distillation take place at low temperatures, such as below 150° C., preferably below 140° C., and more preferably at a temperature in the range of from about 50° C. to about 130° C. Such aldehyde distillation generally takes place under reduced pressure, e.g. a total gas pressure that is substantially lower than the total gas pressure employed during hydroformylation when low boiling aldehydes (e.g. $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium and then pass said volatilized gases and liquid medium which now contains a much lower syn gas concentration than was present in the hydroformylation reaction medium to the distillation zone e.g. vaporizer/separator, wherein the desired aldehyde product is distilled. In general distillation pressures ranging from vacuum pressures or below on up to total gas pressures of about 50 psig should be sufficient for most purposes.

As previously indicated, embodiments of the present invention advantageously minimize or prevent rhodium precipitation by contacting in a reaction zone reactants comprising an olefin, hydrogen and CO in the presence of a rhodium-organophosphite based catalyst, optionally with free organophosphite ligand, and at least one polymer having the structure of Formula (I) or Formula (II) as described further herein. It has been found that such acrylate polymers and polylactones can be employed in embodiments of the present inventions, and such polymers can be homopolymers, copolymers and the like with polar functional groups. In general, the monomers used to form the polymers can include a variety of polar functional groups, though monomers with functional groups that might interfere with the hydroformylation process (e.g., contain thiol moieties, and the like) should generally be avoided.

The polymers useful in embodiments of the present invention comprise functional groups selected from the class consisting of pendant or chain esters and are represented by the structures shown in Formulas (I) and (II), respectively:

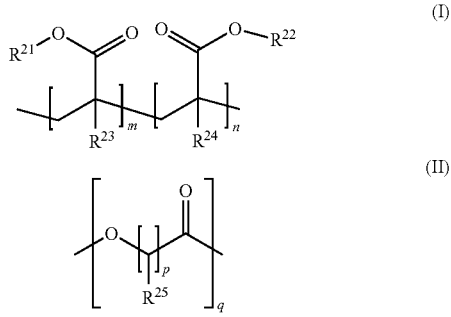

wherein $R^{21}$ and $R^{22}$ are the same or different $C_1$ to $C_{16}$ alkyl or alkyl-substituted aryl moieties and m, n, and q are positive numbers or zero whose sum is greater than 50 and p is 3 to 6 inclusive, wherein the polymer average molecular weight is equal to or above 10,000, wherein $R^{23}$ and $R^{24}$ are H or a $C_1$ to $C_4$ alkyl moiety, wherein $R^{25}$ is H or a $C_1$ to $C_{16}$ alkyl moiety, and wherein $R^{25}$ can be the same or different for each p moiety within Formula (II). The solubility of the polymer having the structure of Formula (I) or Formula (II) in the aldehyde to be produced by the hydroformylation process is greater than or equal to 1 weight percent at 40° C. In some embodiments, the solubility of the polymer having the structure of Formula (I) or Formula (II) in the aldehyde to be produced by the hydroformylation process is greater than or equal to 2 weight percent at 40° C.

Regarding the acrylate polymers in Formula (I), in some embodiments, $R^{21}$ and $R^{22}$ are selected from methyl, ethyl, propyl, butyl, isobutyl, and octyl groups with certain advantageous embodiments having both methyl and butyl moieties for $R^{21}$ and $R^{22}$. $R^{23}$ and $R^{24}$ are H or a $C_1$ to $C_4$ alkyl moiety, with a methyl moiety being particularly advantageous for some embodiments. The acrylate polymers of Formula (I) may be homo, block, or random, and combinations can be utilized in hydroformylation process according to some embodiments, although random acrylate copolymers are preferred. In some embodiments, the acrylate polymer of Formula (I) is poly(butyl methacrylate-co-methyl methacrylate). The acrylate polymer of Formula (I) is poly(isobutylmethacrylate) in some embodiments.

Regarding the polymer of Formula (II), $R^{25}$ is H or a $C_1$ to $C_{16}$ alkyl moiety, wherein $R^{25}$ is the same or different for each p moiety with Formula (II). In some embodiments, $R^{25}$ is H. In some embodiments, where $R^{25}$ is H, p is 5 to 6. In some embodiments, the organic polymer of Formula (II) is polycaprolactone.

The polymers of Formula (I) and (II) are well known and are commercially available from a variety of sources.

The solubility of a polymer in the product aldehyde can be determined as follows. The desired amount of polymer is added to the product aldehyde (e.g., to evaluate the solubility of polycaprolactone in nonanal, polycaprolactone can be added to the nonanal in an amount of 1 weight percent) in a stirred glass vial. The stirred glass vial is placed in a water bath at 40° C. The solubility is determined visually. If the solution is clear and void of solids or turbidity, the polymer is considered soluble at the weight percent at 40° C.

The average molecular weight of such organic polymers does not appear to be narrowly critical and may range from about 10,000 up to 10,000,000 or higher, nor does the amount of the ester moieties on the polymer appear narrowly critical. The preferred organic polymers according to Formula (I) employable as additives in this invention are those containing at least fifty acrylate or methacrylate groups, preferably a mixture of methacrylate groups with at least 10% of the esters as methyl methacrylate moieties, and most preferred are poly(butyl methacrylate-co-methyl methacrylate and polyisobutylacrylate). The nature of these additives generally produces liquid polymers that generate low viscosity solutions in the matrix thus do not interfere with the vaporization process at the levels employed herein.

The amount of such organic polymer additives employable in any given process of this invention need only be that minimum amount necessary to furnish the basis for at least some minimization of such rhodium loss that might be found to occur as a result of carrying out an identical rhodium catalyzed liquid recycle hydroformylation process under identical conditions, save for carrying out said identical process in the absence of the identical organic polymer employed in said given process. Amounts of such organic polymer additives ranging from about 0.1 up to about 3 weight percent based on the total weight of the fluid in the hydroformylation reaction zone should be sufficient for most processes. The upper amount of organic polymer additive employable herein is governed primarily by the solubility limit of the organic polymer in the non-volatilized liquid rhodium catalyst containing residue obtained after distillation removal of as much of the aldehyde product desired. In general, the amount of such organic polymer additives is in the range of about 0.1 to about 3.0 with about 0.25 to about 2.5 weight percent being desirable in some embodiments, each based on the total weight of the fluid in the hydroformylation reaction zone.

The ability to employ such low amounts of the polymer additive useful herein to minimize or prevent rhodium precipitation from solution is an important beneficial aspect of this invention in that such small amounts of additives are far less likely to unduly adversely affect the composition of the rhodium catalyst and/or hydroformylation process as might occur with large amounts of additives.

The addition of the polymer additives employable in this invention to the hydroformylation reaction fluid may be carried out in any suitable manner desired. For instance, the polymer additive (Formula (I) and/or Formula (II)) may be added to the reaction fluid at any time prior to or during the distillation of the aldehyde product therefrom, and may also be removed if desired from the non-volatilized liquid rhodium catalyst containing residue obtained after distillation of as much of the aldehyde product desired, e. g., prior to or during the recycling of said non-volatilized liquid rhodium catalyst containing residue so as to maintain the hydroformylation reaction medium present in the hydroformylation reactor free of such organic polymer additives. However, since it is not believed that such polymer additives will normally have any substantial detrimental effect on the hydroformylation reaction per se. In general, it is preferred to add such polymer additives directly to the hydroformylation reaction fluid and allow the organic polymer additive to remain in solution throughout the entire liquid catalyst recycle hydroformylation solution. Indeed if one has reason to believe that such rhodium precipitation as discussed herein will undoubtedly occur during the desired liquid catalyst recycle hydroformylation process it may be desirable to add the organic polymer to the precursor catalyst solution to be employed so that such organic polymer additives are present right from the start of the hydroformylation process.

Some embodiments of the invention will now be described in more detail in the following Examples.

EXAMPLES

The accelerated testing procedure used in U.S. Pat. No. 4,774,361 is employed to demonstrate the benefits of embodiments of the present invention and comprises subjecting a solubilized activated rhodium-phosphite complex catalyst solution to much harsher conditions than would be experienced during the distillative recovery of aldehyde product during continuous liquid recycle hydroformylation, in order to obtain meaningful results in a much shorter and manageable period of time. Rhodium concentration is determined by atomic absorption (AA) using an air/acetylene flame. It has been found that this technique will not reliably quantify clustered rhodium; thus, this method may be used to indicate "rhodium loss" (e.g., undetectable rhodium is clustered or otherwise no longer in solution). Color change (starting from a colorless or light yellow solution), such as darkening or formation of black film or solids is also indicative of rhodium catalyst degradation. The % rhodium lost is determined as the amount of rhodium found in the sampled solution divided by the amount of rhodium in the starting solution times 100.

All parts and percentages in the following examples are by weight unless otherwise indicated. Pressures are given as absolute pressure unless otherwise indicated.

Solubility studies are performed using C9 aldehydes produced from a mixed octene feed or purchased from Aldrich and used as received. The ligand used is tris(2,4-di-t-butylphenyl) phosphite (hereinafter "Ligand A"). The screening experiments below are conducted in a magnetically stirred glass vial with the specified amount (e.g., 1-3 wt %) of the polymer additive in the C9 aldehyde at ambient temperature and in water baths at 40° C. (taken as typical vaporizer tails temperature which typically is the most concentrated and lowest temperature condition for a continuously operated catalyst solution). For PVP-VA polymers, the ratio listed refers to the relative amounts of polyvinylpyrrolidone:vinyl acetate. Solubility was determined visually based on clear solutions void of solids or turbidity. The results are summarized in Table 1.

TABLE 1

| Polymer | Ave MW | 1 wt. % soluble in C9 aldehyde at 40° C. |
|---|---|---|
| PVP-VA 1.3:1 | 50 K | N |
| PVP-VA 50:50 | | N |
| PVP-VA 30:70 | | N |
| PVP-VA 70:30 | | N |
| PVP-co-styrene | | N |
| PVP-graft-(1-triacontene) | | N |
| poly(methyl methacrylate) | 15 K | N |
| polyvinyltoluene-co-α-styrene | | Y |
| poly(butyl methacrylate-co-methyl methacrylate) | 150 K | Y |
| poly(isobutyl)methacrylate | | Y |
| polycaprolactone | | Y |
| poly(vinyl acetate) | | N |
| Agrimer AL 22 (alkylated PVP) | | Y |
| 1-octyl-2-pyrrolidone | | Y |

Comparative Examples 1-8 and Inventive Examples 1-7

General Procedure: Rhodium Loss Under Representative Vaporizer Conditions:

To evaluate rhodium loss, 90 ml Fisher Porter bottles that are equipped with a sampling port, inlet/outlet valve, and pressure gauge are used as reaction vessels. The Fisher Porter bottles are initially inerted with $N_2$ unless otherwise indicated and are heated in a temperature controlled oil bath. To a solution of the polymer additive in tetraethylene glycol dimethyl ether (20 ml) at 110° C. is added a stock solution of Ligand A in toluene followed by a toluene stock solution of dicarbonyl acetoacetonato-rhodium (I). The ratio of Ligand A to rhodium is 10:1.

This solution is then mixed by flowing 1:1 $CO:H_2$ at 150 psi for 30-60 minutes to generate an active Rh-Ligand A complex. The total pressure is then reduced to 10 psi and held constant at temperature without agitation. Samples are removed periodically and analyzed for rhodium content by air/acetylene atomic absorption (AA) as described above. It has been established that this analytical technique will not reliably quantify clustered rhodium (nor any rhodium that has plated out or precipitated); thus, a decline in detectable rhodium is indicative of "rhodium loss" for this study.

In Comparative Examples 1 and 6-8, the above procedure is followed except that no polymeric additive is used. In Comparative Examples 2-5 and Inventive Examples 1-7, the above procedure is followed with the specified amount of polymer being used. The rhodium loss results are summarized in Tables 2 and 3.

TABLE 2

|  | Initial [Rh] ppm by AA | Additive | [Additive] (wt. %) | [Rh] ppm after 1 days | [Rh] ppm after 2 days | Rh] ppm after 3 days | % [Rh] after 3 days |
|---|---|---|---|---|---|---|---|
| Comp. Ex. 1 | 279 | None (Control) | NA | 234 | 191 | 167 | 59.9 |
| Comp. Ex. 2 | 260 | Poly(vinyltoluene-co-α-methyl styrene) | 1 | 219 | 188 | 176 | 67.7 |
| Inv. Ex. 1 | 260 | Poly(butyl methacrylate-co-methyl methacrylate) | 1 | 245 | 231 | 220 | 84.6 |
| Comp. Ex. 3 | 249 | Agrimer AL 22 (alkylated PVP) | 1 | 162 | 136 | 118 | 47.4 |
| Comp. Ex. 4 | 261 | Agrimer AL 22 (alkylated PVP) | 3 | 169 | 136 | 117 | 44.8 |
| Comp. Ex. 5 | 234 | 1-Octyl-2-pyrrolidone | 1 | 205 | 182 | 170 | 72.6 |

Additional results for poly(butyl methacrylate-co-methyl methacrylate) at higher concentrations are summarized in Table 3.

TABLE 3

|  | Initial [Rh] ppm by AA | Additive | [Additive] (wt. %) | [Rh] ppm after 1 days | [Rh] ppm after 2 days | Rh] ppm after 3 days | % [Rh] after 3 days |
|---|---|---|---|---|---|---|---|
| Comp. Ex. 6 | 267 | None (Control) | NA | 206 | 163 | 140 | 52.4 |
| Inv. Ex. 2 | 266 | Poly(butyl methacrylate-co-methyl methacrylate) | 1.5 | 247 | 237 | 220 | 82.7 |
| Inv. Ex. 3 | 271 | Poly(butyl methacrylate-co-methyl methacrylate) | 2 | 253 | 236 | 217 | 80.1 |

Additional results for other polymers that can be used in embodiments of the present invention are summarized in Tables 4 and 5.

TABLE 4

|  | Initial [Rh] ppm by AA | Additive | [Additive] (wt. %) | [Rh] ppm after 1 days | [Rh] ppm after 5 days | % [Rh] after 5 days |
|---|---|---|---|---|---|---|
| Comp. Ex. 7 | 292 | None (Control) | NA | 263 | 208 | 71.2 |
| Inv. Ex. 4 | 274 | Polycaprolactone | 0.5 | 276 | 261 | 95.3 |
| Inv. Ex. 5 | 274 | Polycaprolactone | 1.0 | 281 | 266 | 97.1 |

TABLE 5

|  | Initial [Rh] ppm by AA | Additive | [Additive] (wt. %) | [Rh] ppm after 1 days | [Rh] ppm after 4 days | % [Rh] after 4 days |
|---|---|---|---|---|---|---|
| Comp. Ex. 8 | 297 | None (Control) | NA | 279 | 211 | 71.0 |
| Inv. Ex. 6 | 297 | Poly(isobutyl)methacrylate | 0.5 | 292 | 280 | 94.3 |
| Inv. Ex. 7 | 290 | Poly(isobutyl)methacrylate | 1.0 | 289 | 278 | 95.9 |

Inventive Example 8

In this example, the use of 1 weight percent poly(butyl methacrylate-co-methyl methacrylate) in a hydroformylation process is evaluated relative to a control without an additive.

The hydroformylation process is conducted in a single-pass glass pressure reactor operating in a continuous mode. The reactor consists of a three ounce Fischer-Porter pressure bottle partially submersed in an oil bath with a glass front for viewing. After purging the system with nitrogen, about 20-30 mL of a freshly prepared rhodium catalyst precursor solution is charged to the reactor with a syringe. The catalyst precursor solution contains about 100-200 ppm rhodium (introduced as rhodium dicarbonyl acetylacetonate), Ligand A, and tetraethylene glycol dimethyl ether as solvent. After sealing the reactor, the system is purged with nitrogen and the oil bath is heated to furnish the desired hydroformylation reaction temperature. The hydroformylation reaction is conducted at a total pressure of 150 to 160 psig (1034 to 1103 kPa) and at a temperature ranging from 60 to 100° C. A feed comprising nitrogen, syngas, and propylene is started. The flows of the feed gases ($H_2$, CO, propylene, $N_2$) are controlled individually with mass flow meters and the feed gases are dispersed in the catalyst precursor solution via fritted metal spargers. The partial pressures of $N_2$, $H_2$, CO, propylene, and aldehyde products are determined by analyzing the vent stream by GC analysis and Dalton's Law. The unreacted portion of the feed gases is stripped out the products by the nitrogen flow to maintain substantially constant liquid level. Flows and feed gas partial pressures are set to obtain hydroformylation reaction rates of around 0.5 to 1 gram-moles aldehyde per liter reaction fluid per hour. To adjust for variations in olefin partial pressures with time, the observed rate is divided to the olefin partial pressure, presuming the kinetics are first order in olefin. The outlet gas is analyzed continuously by GC. In practice, it is often observed that the system takes about one day to arrive at steady state conditions due to removing trace air from feed lines and reaching thermal equilibration of oil baths.

The operating conditions are given below in Table 6 and the results are shown in Table 7.

TABLE 6

| Solvent | Tetraglyme (20 ml) |
|---|---|
| Rhodium concentration | 50 ppm |
| Ligand A | 10 equivalents/Rh |
| Total Pressure | 150 psig |
| CO partial pressure | 50 psig |
| H2 partial pressure | 50 psig |
| Propylene partial pressure | 4 psig |
| Nitrogen partial pressure | Balance |
| Temperature | 75° C. |

TABLE 7

| | Average results (2 days) | |
|---|---|---|
| Experiment | Rate/(Olefin partial pressure) | N:I |
| Inv. Ex. 8 | 0.5238 | 1.03 |
| Control (no additive) | 0.5378 | 1.03 |

As shown in table 7, the presence of 1% poly(butyl methacrylate-co-methyl methacrylate) (based on total catalyst solution) had no detrimental impact on the hydroformylation performance within experimental error. In other words, the polymer was not a catalyst inhibitor or poison.

What is claimed is:

1. A hydroformylation process for producing an aldehyde, the process comprising: contacting in a reaction zone reactants comprising an olefin, hydrogen and CO in the presence of a rhodium-organophosphite based catalyst, optionally with free organophosphite ligand, and 0.1 to 3 weight percent, based on the total weight of the fluid in the reaction zone, of at least one polymer having the structure of Formula (I) or Formula (II), respectively:

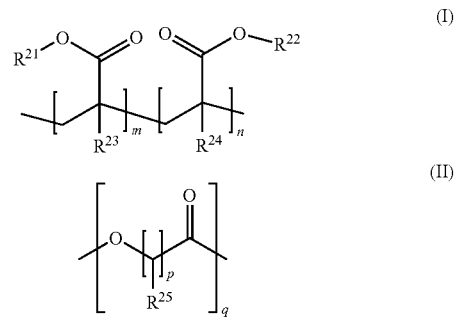

wherein $R^{21}$ and $R^{22}$ are the same or different $C_1$ to $C_{16}$ alkyl or alkyl-substituted aryl moieties and m, n, and q are positive numbers or zero whose sum is greater than 50 and p is 3 to 6 inclusive, wherein the polymer average molecular weight is equal to or above 10,000, wherein $R^{23}$ and $R^{24}$ are H or a $C_1$ to $C_4$ alkyl moiety, wherein $R^{25}$ is H or a $C_1$ to $C_{16}$ alkyl moiety, and wherein $R^{25}$ can be the same or different for each p moiety within Formula (II), such that the solubility of the polymer in the aldehyde is greater than or equal to 1 weight percent at 40° C.

2. The process of claim 1 wherein the olefin is $C_4$ and higher.

3. The process of claim 1 wherein the olefin is $C_8$ and higher.

4. The process of claim 1, wherein $R^{23}$ and $R^{24}$ are methyl.

5. The process of claim 1 wherein the polymer comprises poly(butyl methacrylate-co-methyl methacrylate) or poly(isobutylmethacrylate).

6. The process of claim 1 wherein the polymer comprises polycaprolactone.

7. The process in claim 1 wherein the rate of rhodium loss from the reaction fluid in the hydroformylation process is less than rate of the rhodium loss in a reaction fluid in a hydroformylation process without the polymer additive.

8. The process of claim 7, wherein the rate of rhodium loss from the reaction fluid in the hydroformylation process is at least 20% less than the rate of rhodium loss in a reaction fluid in a hydroformylation process without the polymer additive.

9. The process of claim 1, wherein the polymer is present in the separation zone.

* * * * *